(12) United States Patent
Bhandari et al.

(10) Patent No.: US 11,980,622 B1
(45) Date of Patent: *May 14, 2024

(54) OXCARBAZEPINE EXTENDED RELEASE DOSAGE FORM

(71) Applicant: Apotex Inc., Toronto (CA)

(72) Inventors: Krishna Hari Bhandari, Brampton (CA); Sandeep Patel, Brampton (CA); Navin Vaya, Woodbridge (CA); Bernard Charles Sherman, Toronto (CA); Arunprasath Kaliaperumal, Weston, FL (US)

(73) Assignee: Apotex Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/695,881

(22) Filed: Mar. 16, 2022

Related U.S. Application Data

(63) Continuation of application No. 17/217,178, filed on Mar. 30, 2021, now abandoned.

(60) Provisional application No. 63/040,014, filed on Jun. 17, 2020.

(51) Int. Cl.
| | |
|---|---|
| *A61K 9/28* | (2006.01) |
| *A61K 9/00* | (2006.01) |
| *A61K 9/20* | (2006.01) |
| *A61K 31/55* | (2006.01) |

(52) U.S. Cl.
CPC ............ *A61K 31/55* (2013.01); *A61K 9/0053* (2013.01); *A61K 9/2054* (2013.01); *A61K 9/2095* (2013.01)

(58) Field of Classification Search
None
See application file for complete search history.

(56) References Cited

U.S. PATENT DOCUMENTS

| | | | |
|---|---|---|---|
| 6,296,873 B1 * | 10/2001 | Katzhendler | A61K 9/2054 424/464 |
| 7,722,898 B2 | 5/2010 | Bhatt et al. | |
| 7,910,131 B2 | 3/2011 | Bhatt et al. | |
| 8,617,600 B2 | 12/2013 | Bhatt et al. | |
| 8,821,930 B2 | 9/2014 | Bhatt et al. | |
| 9,119,791 B2 | 9/2015 | Bhatt et al. | |
| 9,351,975 B2 | 5/2016 | Bhatt et al. | |
| 9,370,525 B2 | 6/2016 | Bhatt et al. | |
| 9,855,278 B2 | 1/2018 | Bhatt et al. | |
| 10,220,042 B2 | 3/2019 | Bhatt et al. | |
| 2002/0169145 A1 * | 11/2002 | Shah | A61P 9/10 514/460 |
| 2006/0068010 A1 * | 3/2006 | Turner | A61K 9/2054 424/469 |
| 2007/0059354 A1 * | 3/2007 | Ramakrishnan | A61K 9/2027 514/217 |
| 2008/0138403 A1 * | 6/2008 | Mungre | A61K 9/2054 514/217 |
| 2008/0260836 A1 * | 10/2008 | Boyd | A61Q 11/00 424/70.13 |
| 2009/0196919 A1 | 8/2009 | Singla et al. | |
| 2017/0059354 A1 | 3/2017 | Colby | |

FOREIGN PATENT DOCUMENTS

| | | | | |
|---|---|---|---|---|
| CN | 106727391 A | * | 5/2017 | ............ A61K 31/55 |
| CN | 109010322 A | * | 12/2018 | ............ A61K 31/55 |
| IN | 3426/MUM/2013 A | | 7/2015 | |
| WO | 2015063670 A1 | | 5/2015 | |

OTHER PUBLICATIONS

"Remington: The Science and Practice of Pharmacy", Lippincott Williams & Wilkins, 2005, 2 pages.

* cited by examiner

*Primary Examiner* — Susan T Tran

(74) *Attorney, Agent, or Firm* — The Webb Law Firm

(57) ABSTRACT

The present invention relates to extended release pharmaceutical dosage forms of oxcarbazepine.

23 Claims, 1 Drawing Sheet

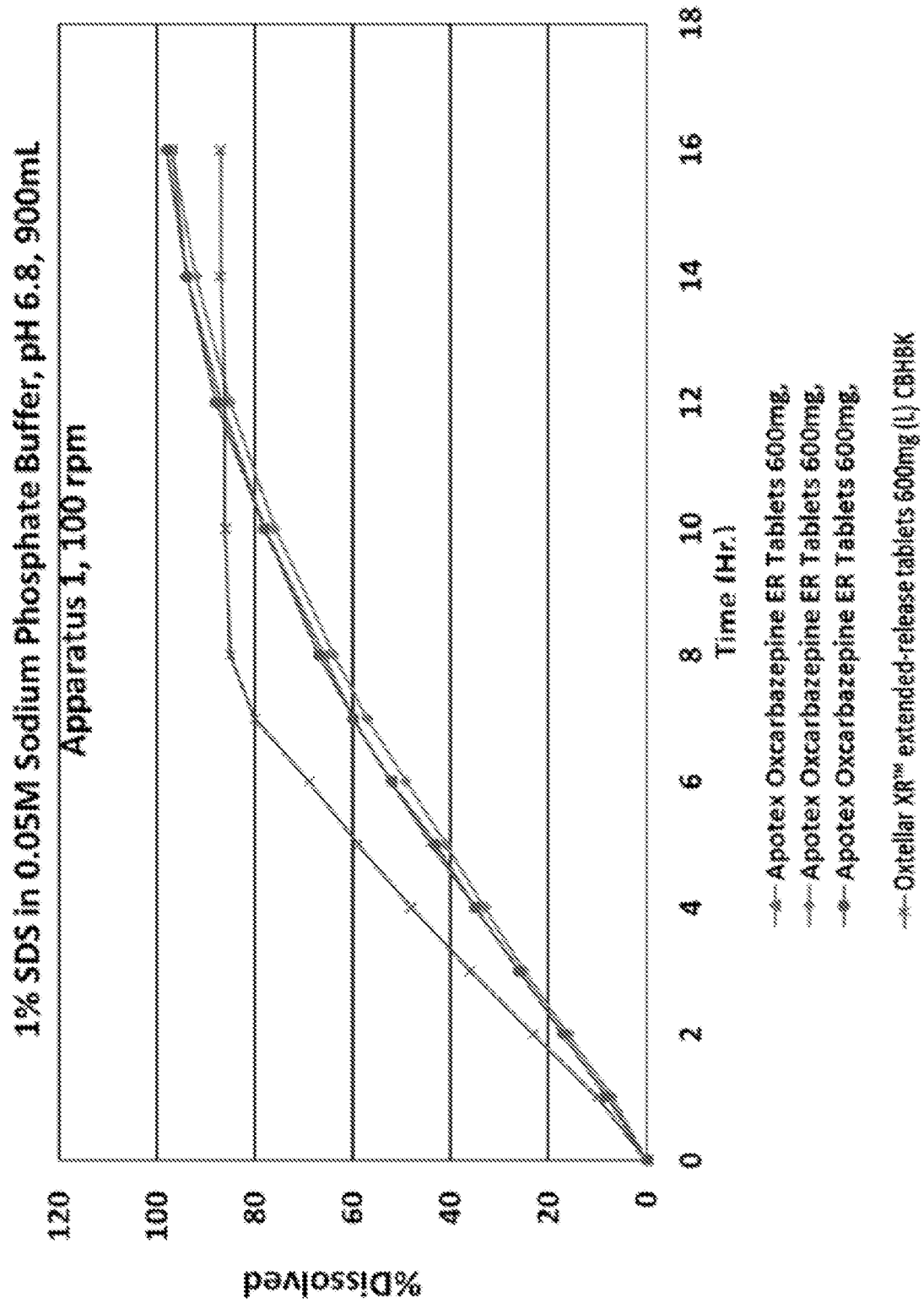

OXCARBAZEPINE EXTENDED RELEASE DOSAGE FORM

CROSS-REFERENCE TO RELATED APPLICATIONS

This application is a continuation of U.S. patent application Ser. No. 17/217,178, filed Mar. 30, 2021, which claims the benefit of U.S. Provisional Application Ser. No. 63/040,014, filed Jun. 17, 2020, each of which are incorporated by reference herein in their entireties.

BACKGROUND OF THE INVENTION

Field of the Invention

The present invention relates to an extended release pharmaceutical dosage form of oxcarbazepine.

Description of Related Art

Oxcarbazepine is an antiepileptic medication that is indicated in the United States as an adjunctive therapy in the treatment of partial seizures in both adults and children. Oxcarbazepine is sold in both an immediate release formulation (Trileptal®) and an extended release formulation (Oxtellar XR®). The extended release formulation provides for greater patient compliance by reducing the number of times the drug must be taken each day. Oxtellar XR® is available in strengths of 150 mg, 300 mg and 600 mg extended release tablets.

A number of different extended release formulations of oxcarbazepine are disclosed in the art.

The formulations specifically relevant to Oxtellar XR® are disclosed in U.S. Pat. Nos. 7,722,898, 7,910,131, 8,617,600, 8,821,930, 9,119,791, 9,351,975, 9,370,525, 9,855,278 and 10,220,042, which are all listed in the FDA's Orange Book of approved drug products. Such formulations require tablets to comprise oxcarbazepine, a matrix-forming polymer, at least one agent that enhances the solubility of oxcarbazepine, and at least one release promoting agent comprising a polymer having a pH-dependent solubility.

US 2017/0059354 discloses sustained release dosage forms of oxcarbazepine that require the presence of hydroxypropyl methylcellulose (HPMC) having a specific viscosity range. The tablets disclosed therein comprise oxcarbazepine and HPMC that has a viscosity of 11,000 to 25,000 cps.

Indian patent application 3426/MUM/2013 discloses modified release compositions comprising oxcarbazepine. The compositions disclosed are highlighted in that they are devoid of excipients having pH-dependent solubility. However, in the example provided, the formulation required the presence of an agent that enhances the solubility of oxcarbazepine, specifically, the surfactant sodium lauryl sulphate.

WO2015/063670 discloses modified release compositions comprising oxcarbazepine. The compositions are characterized by a core comprising oxcarbazepine and excipients that is coated with a functional coating. The functional coating comprises one or more excipients having pH-dependent solubility.

US 2009/0196919 discloses dosage forms of oxcarbazepine having a median particle size of from about 14 μm to about 30 μm. The application appears to disclose immediate release dosage forms.

SUMMARY

The present invention provides oral extended-release dosage forms of oxcarbazepine, and processes for the production of oral extended-release dosage forms of oxcarbazepine.

In one embodiment, the present invention provides an extended release dosage form of oxcarbazepine for oral administration comprising oxcarbazepine, HPMC that has a viscosity below 11,000 cP and one or more additional pharmaceutically acceptable excipients.

In a preferred embodiment of the present invention the weight percentage of HPMC is between 20% and 65%.

In another embodiment, the HMPC has a viscosity ranging between 50 and 500 cP.

In another embodiment, the HMPC has a viscosity ranging between 80 and 120 cP.

In another embodiment, the oxcarbazepine used in the production of the dosage form has a particle size diameter range with a D90 of not more than 110 μm, a D50 of not more than 55 μm and a D10 of not more than 25 μm.

In a preferred embodiment, the composition is in the form of a tablet. In a further preferred embodiment, the total amount of oxcarbazepine in the composition is from about 150 mg to about 600 mg of oxcarbazepine. In a further preferred embodiment, the total amount of oxcarbazepine in the composition is at least one of the following:

150 mg, 300 mg and 600 mg.

The details of one or more embodiments of the present invention are set forth in the description below. Other features, objects and advantages of the inventions will be apparent from the description and claims.

BRIEF DESCRIPTION OF THE DRAWINGS

FIG. 1 is a graph showing dissolution of tablets according to non-limiting embodiments or aspects as described herein.

DETAILED DESCRIPTION

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

The use of numerical values in the various ranges specified in this application are stated as approximations as though the minimum and maximum values within the stated ranges are both preceded by the word "about". In this manner, slight variations (e.g., 10%) above and below the stated ranges can be used to achieve substantially the same results as values within the ranges. Also, unless indicated otherwise, the disclosure of ranges is intended as a continuous range including every value between the minimum and maximum values. Further, as used herein, all numbers expressing dimensions, physical characteristics, processing parameters, quantities of ingredients, reaction conditions, and the like, used in the specification and claims are to be understood as being modified in all instances by the term "about". Moreover, unless otherwise specified, all ranges disclosed herein are to be understood to encompass the beginning and ending range values and any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 3.3, 4.7 to 7.5, 5.5 to 10, and the like.

As used herein "a" and "an" refer to one or more. The term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention.

Although extended-release formulations of oxcarbazepine are known, these known formulations require at least one agent that enhances the solubility of oxcarbazepine, and at least one release promoting agent.

The present invention provides novel extended-release oxcarbazepine dosage forms, which allow for once-daily oral administration. The extended-release dosage forms of the present invention are bioequivalent to the currently marketed Oxtellar XR® tablets but are different because they provide for a simplified formulation for manufacturing purposes. As a result, the dosage forms of the present invention provide for the extended release of oxcarbazepine while also avoiding the use of certain excipients in the formulation.

Oxtellar XR® tablets require the presence of both a polymer having pH-dependent solubility (methacrylic acid copolymer) and an agent that enhances the solubility of oxcarbazepine (sodium lauryl sulfate). The present invention provides dosage forms without requiring the addition of a polymer having pH-dependent solubility.

It has been found that for oxcarbazepine extended release dosage forms of the present invention that despite the poor solubility of oxcarbazepine, it is possible to produce matrix-type tablets that only require the presence of a matrix forming polymer, and do not need require the inclusion of a polymer having pH-dependent solubility.

The tablet of the present invention, will preferably, when dissolution tested using USP Apparatus 1, exhibit a release profile substantially corresponding to the following pattern:
after 5 hours at 100 rpm in 900 mL of 1% SDS in 0.05 M Sodium phosphate buffer, pH 6.8, at a temperature of 37° C.±0.5° C., at least about 28% by weight of the total oxcarbazepine is released, or from about 28% by weight to about 53% by weight of the total oxcarbazepine is released, and
after 8 hours at 100 rpm in 900 mL of 1% SDS in 0.05 M Sodium phosphate buffer, pH 6.8, at a temperature of 37° C.±0.5° C., at least about 50% by weight of the total oxcarbazepine is released, or from about 50% by weight to about 76% by weight of the total oxcarbazepine is released.

Some tablets of the present invention, will preferably, when dissolution tested using USP Apparatus 1, exhibit a release profile substantially corresponding to the following pattern:
after 2 hours at 100 rpm in 900 mL of 1% SDS in 0.05 M Sodium phosphate buffer, pH 6.8, at a temperature of 37° C.±0.5° C., no more than about 25% by weight of the total oxcarbazepine is released, and
after 5 hours at 100 rpm in 900 mL of 1% SDS in 0.05 M Sodium phosphate buffer, pH 6.8, at a temperature of 37° C.±0.5° C., at least about 28% by weight of the total oxcarbazepine is released, or from about 28% by weight to about 53% by weight of the total oxcarbazepine is released,
after 8 hours at 100 rpm in 900 mL of 1% SDS in 0.05 M Sodium phosphate buffer, pH 6.8, at a temperature of 37° C.±0.5° C., at least about 50% by weight of the total oxcarbazepine is released, or from about 50% by weight to about 76% by weight of the total oxcarbazepine is released, and
after 16 hours at 100 rpm in 900 mL of 1% SDS in 0.05 M Sodium phosphate buffer, pH 6.8, at a temperature of 37° C.±0.5° C., not less than about 80% by weight of the total oxcarbazepine is released.

Some tablets of the present invention, will preferably, when dissolution tested using USP Apparatus 1 at 100 rpm in 900 mL of 1% SDS in 0.05 M Sodium phosphate buffer, pH 6.8, at a temperature of 37° C.±0.5° C., exhibit a release profile substantially corresponding to the following pattern:

| | Dissolution Profile | |
|---|---|---|
| | 150 or 300 mg oxcarbazepine tablet | 600 mg oxcarbazepine tablet |
| | Weight percent of total oxcarbazepine released | |
| 2 hr | Not more than 25 | Not more than 25 |
| 5 hr | 28-48 | 33-53 |
| 8 hr | 50-70 | 56-76 |
| 16 hr | Not less than 80 | Not less than 80 |

In addition, the dosage forms of the present invention utilize oxcarbazepine that is characterized by a particle size distribution wherein D10 is not more than 25 μm, D50 is not more than 55 μm and D90 is not more than 110 μm. Using oxcarbazepine with this particle size distribution helps to overcome the drug insolubility issues associated with the compound.

In one embodiment of the present invention, the rate controlling polymer used in the present invention is hydroxypropyl methylcellulose (HPMC), wherein the HPMC has a viscosity (USP-NF method) of less than 11000 cP. In a preferred embodiment, the HPMC has a viscosity of less than 6000 cP. In another preferred embodiment, the HPMC has a viscosity of 50 to 6000 cP. In another preferred embodiment, the HPMC has a viscosity of 50 to 5000 cP. In another preferred embodiment, the HPMC has a viscosity of 50 to 4000 cP. In another preferred embodiment, the HPMC has a viscosity of 50 to 3000 cP.

In another preferred embodiment, the HPMC has a viscosity of 50 to 2000 cP. In another preferred embodiment, the HPMC has a viscosity of 50 to 1000 cP. In another preferred embodiment the HPMC has a viscosity of 50 to 500 cP. In another preferred embodiment, the HPMC has a viscosity of 50 to 250 cP. In a further preferred embodiment, the HPMC used as the rate controlling polymer has a viscosity ranging between 80 to 120 cP.

Non-limiting examples of suitable HPMC include Type 1828, Type 2208, Type 2906, Type 2910, or mixtures thereof.

In a preferred embodiment of the present invention, the weight percentage of HPMC can range from about 20% to about 65%.

The extended release dosage forms of the present invention may include one or more additional pharmaceutically acceptable excipients comprising fillers/diluents, lubricants, glidants, flavouring agents, colouring agents and the like.

The phrase "pharmaceutically acceptable excipient" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material. Each excipient must be "acceptable" in the sense of being compatible with the other ingredients of the formulation and not injurious to the subject being treated. Non-limiting examples of materials which can serve as pharmaceutically acceptable excipients are presented in. Remington: The Science and Practice of Pharmacy, The University of the Sciences in Philadelphia, Editor, Lippincott, Williams, & Wilkins, Philadelphia, Pa., 21st Edition (2005), which describes compositions and formulations suitable for pharmaceutical delivery of one or more therapeutic compositions.

Fillers/diluents may be selected from any such pharmaceutically acceptable excipients that gives bulk to the oxcarbazepine composition and improves compressibility. For example, preferable diluents include one or more of calcium carbonate, calcium phosphate-dibasic, calcium phosphate-tribasic, calcium sulfate, cellulose-microcrystalline, cellulose powdered, dextrates, dextrins, dextrose excipients, fructose, kaolin, lactitol, lactose, mannitol, sorbitol, starch, starch pregelatinized, sucrose, sugar compressible, or sugar confectioners. In a preferred embodiment, the filler is sorbitol.

Lubricants may be selected from, for example, one or more of colloidal silicon dioxide, stearic acid, magnesium stearate, calcium stearate, talc, hydrogenated vegetable oil, sucrose esters of fatty acids, microcrystalline wax, yellow beeswax, white beeswax, and glyceryl monostrearate. Other suitable lubricants also may be used separately or in combination.

Glidants may be selected from, for example, colloidal silicon dioxide and talc, although any other suitable glidants may be used.

The dosage form may optionally be coated with functional and/or non-functional layers comprising film-forming polymers. The coating composition may include polymers and other coating additives.

Examples of film-forming polymers include polyvinyl alcohol, ethylcellulose, hydroxypropyl methylcellulose, hydroxypropylcellulose, methylcellulose, carboxymethyl cellulose, hydroxymethylcellulose, hydroxyethylcellulose, cellulose acetate, hydroxypropyl methylcellulose phthalate, cellulose acetate phthalate, cellulose acetate trimellitate; waxes such as polyethylene glycol; and the like. Alternatively, commercially available coating compositions comprising film-forming polymers marketed under various trade names, such as Opadry® may also be used for coating. Coating additives may be selected from, for example, plasticizers, coloring agents, gloss producer, lubricants/glidants.

Polymer solution or dispersion may be prepared in various solvents such as water, ethanol, methanol, isopropyl alcohol, chloroform, acetone, ether or mixtures thereof. The coating composition can be coated onto solid dosage form using techniques such as spray coating in conventional coating pan or fluidized bed processor, or dip coating.

The extended release dosage forms of the present invention may be in the form of granules, pellets, tablets, capsules, granules, pellets and/or tablets filled in capsule, or a multilayer tablet. Preferably, the dosage form is in the form of a tablet.

The dosage forms of the present invention may be used for the treatment of epileptic seizures. In particular, the dosage forms of the present invention may be used as an adjunctive therapy in the treatment of partial seizures in both adults and children.

In preferred embodiments of the present invention, each of the tablets will contain about 150 mg to about 600 mg of oxcarbazepine. In a more preferred embodiment of the composition, the total amount of oxcarbazepine in each of the tablets is 150 mg, 300 mg or 600 mg.

According to one aspect of the present invention, there is provided an extended release dosage form of oxcarbazepine wherein the dosage form comprises:
a) oxcarbazepine;
b) low viscosity HPMC;
c) a filler;
and additionally, one or more glidants and lubricants.

According to one aspect of the present invention, there is provided an extended release dosage form of oxcarbazepine wherein the dosage form comprises:
a) about 25-60% by weight of oxcarbazepine;
b) about 20-65% by weight of low viscosity HPMC;
c) about 5-20% by weight of a filler;
and additionally, one or more glidants and lubricants.

According to one aspect of the present invention, there is provided an extended release dosage form of oxcarbazepine wherein the dosage form comprises:
a) oxcarbazepine;
b) low viscosity HPMC;
c) colloidal silicon dioxide;
d) magnesium stearate;
e) sorbitol; and
f) talc.

According to one aspect of the present invention, there is provided an extended release dosage form of oxcarbazepine wherein the dosage form comprises:
a) about 25-60% by weight oxcarbazepine;
b) about 20-65% by weight of low viscosity HPMC;
c) about 0.9-0.14% by weight of colloidal silicon dioxide;
d) about 0.4-0.6% by weight of magnesium stearate;
e) about 5-20% sorbitol; and
f) talc.

In non-limiting embodiments, the extended release dosage form is substantially free of, or free of, any release promoting agents, such as cellulose acetate phthalate, cellulose acetate succinate, methylcellulose phthalate, ethylhydroxycellulose phthalate, polyvinylacetate phthalate, polyvinylbutyrate acetate, vinyl acetate-maleic anhydride copolymer, styrene-maleic mono-ester copolymer, and methacrylic acid copolymers such as Eudragit L100-55 (Methacrylic Acid-Ethyl Acrylate Copolymer (1:1)), and methyl acrylate-methacrylic acid copolymers. As used herein, "substantially free of release promoting agents" means that the extended release dosage form comprises less than about 5 weight percent, or less than about 1 weight percent, of any of the release promoting agents.

In a further preferred embodiment of the present invention, the oral dosage form provides equivalent $AUC_T$ and $C_{max}$ levels to those provided by Oxtellar XR® tablets.

$AUC_T$ as used herein is defined as the area under the curve of serum concentration versus time for a chosen period of time after ingestion, such as, for example 24 hours. $AUC_T$ ratio as used herein is defined as the ratio of mean $AUC_T$ provided by the test product to the mean $AUC_T$ provided by the reference product.

$C_{max}$ as used herein is defined as the peak serum concentration. $C_{max}$ ratio as used herein is defined as the ratio of $C_{max}$ from the test product to $C_{max}$ from the reference product, also calculated for each subject.

Oral dosage forms of the present invention are considered to provide equivalent $AUC_T$ and $C_{max}$ levels to those provided by Oxtellar XR® tablets if the $C_{max}$ and $AUC_T$ ratios are within the range of 80% to 125%, all values and subranges there between inclusive.

The present invention will be better understood from the following examples, which are intended to be illustrative of the invention and not limiting. It will be apparent to a person of skill in the art that various alterations may be made when using the compositions and methods of the present invention without departing from the scope or intent thereof.

EXAMPLES

The following non-limiting examples are illustrative of some of the aspects and embodiments of the invention described herein.

Example 1

Ingredients for a 130.6 kg batch were dispensed as follows:

| Ingredients | Qty (kg) |
|---|---|
| OXCARBAZEPINE | 76.8 |
| SORBITOL | 13.7 |
| HYDROXYPROPYL METHYLCEL. 2208 K100LV | 35.2 |
| COLLOIDAL SILICON DIOXIDE | 0.154 |
| MAGNESIUM STEARATE (PART 1) | 0.62 |
| SUB TOTAL | 126.5 |
| MAGNESIUM STEARATE (PART 2) | 1.28 |
| TALC | 0.26 |
| CORE TOTAL | 128.0 |
| FILM COATING INGREDIENTS | 2.6 |
| COATED TOTAL | 130.6 |

The oxcarbazepine, colloidal silicon dioxide, magnesium stearate (Part 1), Hydroxypropyl Methylcellulose 0.2208 K100Iv and Sorbitol were screened, mixed, compacted and milled. After milling, MAGNESIUM STEARATE (PART 2) and TALC were then added, and the material was mixed. This final mixture was then compressed into tablets and film coated.

The tablets, when dissolution tested using USP Apparatus #1, 100 rpm, Media: 900 mL of 1% SDS in 0.05 M Sodium phosphate buffer, pH 6.8, at a temperature of 37° C.±0.5° C. were found to comply with the following specifications:

| Time | Mean % Dissolved |
|---|---|
| 2 hrs (120 min) | NMT 25% |
| 5 hrs(300 min) | 27-52%; |
| 8 hrs (480 min) | 50-75% |
| 14 hrs (960 min) | NLT 85% |

Dissolution of 600 mg tablets is shown in FIG. 1.

In a comparative bioavailability study in 103 subjects in the fed state, the mean results, as a ratio of the parameters for the tablets of Example 1 and the OXTELLAR XR® 600 5 mg tablet where:
AUCt ratio: 99.4%
Cmax ratio: 94.4%

In a comparative bioavailability study in 82 subjects in the fasting state, the mean results, as a ratio of the parameters for the tablets of Example 1 and the OXTELLAR XR® 600 mg tablet were:
AUCt ratio: 94.3%
Cmax ratio: 102.7%

Based the results of the bioequivalence studies, the above tablets were considered bioequivalent to the commercially available OXTELLAR XR® tablets.

Example 2

The below table provides examples of tablets of the present invention formulated in strengths of 150 mg, 300 mg and 600 mg.

| Component and its Grade | Quality Standard | Function | Strength 150 mg Quantity (mg) per Unit Dose | Strength 150 mg % w/w total unit dose weight | Strength 300 mg Quantity (mg) per Unit Dose | Strength 300 mg % w/w total unit dose weight | Strength 600 mg Quantity (mg) per Unit Dose | Strength 600 mg % w/w total unit dose weight |
|---|---|---|---|---|---|---|---|---|
| Core | | | | | | | | |
| Oxcarbazepine* | USP | Active | 150 | 29.41 | 300 | 45.25 | 600 | 58.82 |
| Sorbitol Crystalline Fines | NF | Filler | 66 | 12.94 | 63.3 | 9.55 | 107.0 | 10.49 |
| Hydroxypropyl Methylcellulose 2208 K100LV | USP | Matrix forming polymer | 275 | 53.92 | 275 | 41.48 | 275 | 26.96 |
| Colloidal Silicon Dioxide | NF | Glidant | 0.6 | 0.1176 | 0.78 | 0.1176 | 1.200 | 0.1176 |
| Magnesium Stearate (Part 1) | NF | Lubricant | 2.4 | 0.471 | 3.12 | 0.471 | 4.80 | 0.471 |
| Sub-Total | | | 494 | 96.86 | 642.2 | 96.86 | 988 | 96.86 |
| Magnesium Stearate (Part 2) | NF | Lubricant | 5 | 0.980 | 6.5 | 0.980 | 10.0 | 0.980 |
| Talc 500 Mesh | USP | Glidant/ Anti-adhere | 1 | 0.196 | 1.3 | 0.196 | 2.0 | 0.196 |
| TOTAL of Core Coating | | | 500 | 98.03 | 650 | 98.04 | 1000 | 98.03 |
| Polyvinyl Alcohol USP EG-05PW | USP | Film Forming Polymer | 1.92 | 0.376 | 2.5 | 0.377 | 3.2 | 0.313 |

-continued

| Component and its Grade | Quality Standard | Function | Strength 150 mg Quantity (mg) per Unit Dose | Strength 150 mg % w/w total unit dose weight | Strength 300 mg Quantity (mg) per Unit Dose | Strength 300 mg % w/w total unit dose weight | Strength 600 mg Quantity (mg) per Unit Dose | Strength 600 mg % w/w total unit dose weight |
|---|---|---|---|---|---|---|---|---|
| Polyethylene Glycol 8000 | NF | Plasticizer | 1.33 | 0.260 | 1.72 | 0.259 | 2.16 | 0.211 |
| Talc 500 Mesh | USP | Anti-adherent | 6.262 | 1.228 | 5.8 | 0.875 | 8.7 | 0.853 |
| Titanium Dioxide | USP | Opacifier | | | 2.08 | 0.313 | 4.24 | 0.416 |
| Red Ferric Oxide | NF | Colorant | | | 0.4 | 0.060 | 1.70 | 0.1667 |
| Yellow Ferric Oxide | NF | Colorant | 0.488 | 0.095 | 0.4 | 0.060 | | |
| Black Iron Oxide (Ferrosoferric Oxide) | NF | Colorant | | | 0.1 | 0.015 | | |
| PurifiedWater** | USP | Solvent | 40 | | 52 | | 80 | |
| TOTAL | | | 510 | 100 | 663 | 100 | 1020 | 100 |

While the present invention has been described in terms of the above detailed description, those of ordinary skill will understand that alterations may be made within the spirit of the invention. Accordingly, the above should not be considered limiting, and the scope of the invention is defined by the appended claims.

What is claimed is:

1. An extended-release dosage form of oxcarbazepine for oral administration comprising oxcarbazepine, hydroxypropyl methylcellulose (HPMC) that has a viscosity ranging from about 50 to about 500 cP, and one or more additional pharmaceutically acceptable excipients,
   wherein the dosage form is substantially free, or free of, a release promoting agent(s) and/or a polymer(s) having pH-dependent solubility,
   wherein the weight percentage of HPMC is from about 20% to about 65% based upon total weight of the dosage form, and
   wherein the dosage form has $C_{max}$ and AUCT ratios in the range of 80% to 125%, relative to an oxcarbazepine extended-release dosage form comprising a polymer having pH-dependent solubility and having a similar total amount of oxcarbazepine.

2. The dosage form of claim 1, wherein the HMPC has a viscosity ranging from about 80 to about 120 cP.

3. The dosage form of claim 1, wherein the oxcarbazepine used in the production of the dosage form has a particle size diameter range with a D90 of not more than about 110 μm.

4. The dosage form of claim 1, wherein the oxcarbazepine used in the production of the dosage form has a particle size diameter range with a D50 of not more than about 55 μm.

5. The dosage form of claim 1, wherein the oxcarbazepine used in the production of the dosage form has a particle size diameter range with a D10 of not more than about 25 μm.

6. The dosage form of claim 1, wherein the composition is in the form of a tablet.

7. The dosage form of claim 1, wherein the total amount of oxcarbazepine in the composition is from about 150 mg to about 600 mg of oxcarbazepine.

8. The dosage form of claim 1, wherein the total amount of oxcarbazepine in the composition is 150 mg, 300 mg or 600 mg.

9. The dosage form of claim 1, wherein the dosage form is substantially free of release promoting agents.

10. The dosage form of claim 1, wherein the dosage form is free of release promoting agents.

11. The dosage form of claim 1, when dissolution tested using USP Apparatus 1, exhibits a release profile substantially corresponding to the following pattern:
   after 5 hours at 100 rpm in 900 mL of 1% SDS in 0.05 M Sodium phosphate buffer, pH 6.8, at a temperature of 37° C.±0.5° C., at least about 28% by weight of the total oxcarbazepine is released, and
   after 8 hours at 100 rpm in 900 mL of 1% SDS in 0.05 M Sodium phosphate buffer, pH 6.8, at a temperature of 37° C.±0.5° C., at least about 50% by weight of the total oxcarbazepine is released.

12. The dosage form of claim 1, wherein after 5 hours at 100 rpm in 900 mL of 1% SDS in 0.05 M Sodium phosphate buffer, pH 6.8, at a temperature of 37° C.±0.5° C., from about 28% by weight to about 53% by weight of the total oxcarbazepine is released.

13. The dosage form of claim 1, wherein after 8 hours at 100 rpm in 900 mL of 1% SDS in 0.05 M Sodium phosphate buffer, pH 6.8, at a temperature of 37° C.±0.5° C., from about 50% by weight to about 76% by weight of the total oxcarbazepine is released.

14. The dosage form of claim 1, when dissolution tested using USP Apparatus 1, exhibits a release profile substantially corresponding to the following pattern:
   after 2 hours at 100 rpm in 900 mL of 1% SDS in 0.05 M Sodium phosphate buffer, pH 6.8, at a temperature of 37° C.±0.5° C., no more than about 25% by weight of the total oxcarbazepine is released, and
   after 5 hours at 100 rpm in 900 mL of 1% SDS in 0.05 M Sodium phosphate buffer, pH 6.8, at a temperature of 37° C.±0.5° C., at least about 28% by weight of the total oxcarbazepine is released,
   after 8 hours at 100 rpm in 900 mL of 1% SDS in 0.05 M Sodium phosphate buffer, pH 6.8, at a temperature of 37° C.±0.5° C., at least about 50% by weight of the total oxcarbazepine is released, and
   after 16 hours at 100 rpm in 900 mL of 1% SDS in 0.05 M Sodium phosphate buffer, pH 6.8, at a temperature of 37° C.±0.5° C., not less than about 80% by weight of the total oxcarbazepine is released.

15. A method of making an extended-release dosage form of oxcarbazepine having bioequivalence to an oxcarbazepine extended-release dosage form comprising a polymer having pH-dependent solubility and having a similar total amount of oxcarbazepine in the dosage form, comprising:

mixing and milling oxcarbazepine, hydroxypropyl methylcellulose having viscosity ranging from about 50 to about 500 cP, and one or more pharmaceutically acceptable excipients to provide a mixture, wherein the mixture is substantially free, or free of, a release promoting agent(s) and/or a polymer(s) having pH-dependent solubility, wherein the weight percentage of HPMC is from about 20% to about 65% based upon total weight of the dosage form; and compressing the mixture into tablets, wherein the dosage form has $C_{max}$ and AUCT ratios in the range of 80% to 125%, relative to an oxcarbazepine extended-release dosage form comprising a polymer having pH-dependent solubility and having a similar total amount of oxcarbazepine.

16. The method of claim 15, wherein the one or more pharmaceutically acceptable excipients excludes release promoting agents.

17. A method of treating epileptic seizures, comprising administering, to a person in need thereof, the extended release dosage form of claim 1, in an amount effective to reduce the incidence and/or severity of the epileptic seizures.

18. The method of claim 17, wherein the amount effective is 150 mg per day.

19. The method of claim 17, wherein the amount effective is 300 mg per day.

20. The method of claim 17, wherein the effective amount is 600 mg.

21. The method of claim 17, wherein the extended release dosage form is administered once daily.

22. A method of making an extended release dosage form of oxcarbazepine of claim 1, comprising:

mixing and milling oxcarbazepine, hydroxypropyl methylcellulose, and one or more pharmaceutically acceptable excipients to provide a mixture; and compressing the mixture into tablets.

23. The dosage form of claim 1, wherein the dosage form is substantially free, or free of, a polymer(s) having pH-dependent solubility.

* * * * *